(12) United States Patent
Soung

(10) Patent No.: US 8,240,310 B2
(45) Date of Patent: Aug. 14, 2012

(54) MEDICAL POSITIONER HAVING IMMOBILIZER FUNCTION

(76) Inventor: Il-Ho Soung, Seoul (KR)

( * ) Notice: Subject to any disclaimer, the term of this patent is extended or adjusted under 35 U.S.C. 154(b) by 247 days.

(21) Appl. No.: 12/795,873

(22) Filed: Jun. 8, 2010

(65) Prior Publication Data

US 2011/0000494 A1 Jan. 6, 2011

(30) Foreign Application Priority Data

Jul. 6, 2009 (KR) .................. 10-2009-0061167
Mar. 5, 2010 (KR) .................. 10-2010-0019735

(51) Int. Cl.
*A61G 15/00* (2006.01)
*A61B 19/00* (2006.01)
*A61F 5/37* (2006.01)
*A47C 19/22* (2006.01)

(52) U.S. Cl. ........ 128/845; 128/869; 128/873; 128/874; 5/632

(58) Field of Classification Search .................. 128/845, 128/846, 847, 869, 870, 873, 874; 5/632, 5/630, 621, 623, 624, 625, 626, 628; 602/5, 602/6, 13; 601/6, 11
See application file for complete search history.

(56) References Cited

U.S. PATENT DOCUMENTS

| | | | |
|---|---|---|---|
| 3,745,998 A | 7/1973 | Rose | |
| 4,628,913 A | 12/1986 | Lerman | |
| 4,657,003 A | 4/1987 | Wirtz | |
| 6,161,237 A | 12/2000 | Tang et al. | |
| 6,308,353 B1 * | 10/2001 | Van Steenburg | 5/632 |
| 2002/0133877 A1 | 9/2002 | Kuiper et al. | |
| 2004/0016057 A1 | 1/2004 | Traut et al. | |
| 2007/0066922 A1 | 3/2007 | Farley et al. | |
| 2007/0270725 A1 | 11/2007 | Sherman et al. | |

FOREIGN PATENT DOCUMENTS

| | | |
|---|---|---|
| JP | 05-503653 | 6/1993 |
| JP | 07-042631 | 2/1995 |
| JP | 2002-540892 | 12/2002 |

(Continued)

OTHER PUBLICATIONS

Korean Decision of Grant—Korean Application No. 10-2010-0019735 issued on Nov. 30, 2011, citing JP 07-042631 and KR 10-2006-0043399.
European Search Report—European Patent Application No. 10251157.3 issued Oct. 13, 2010.
Japanese Office Action—Japanese Application No. 2010-087716 issued on Feb. 14, 2012, citing JP 2002-540892, WO 2006/081412, JP 2008-033074, JP 05-503653, JP 2009-112380, and JP 2003-534047.

*Primary Examiner* — Patricia Bianco
*Assistant Examiner* — Ophelia Hawthorne
(74) *Attorney, Agent, or Firm* — Cantor Colburn LLP

(57) ABSTRACT

Provided is a medical positioner having an immobilizer function. The medical positioner includes a vacuum pad allowing air to freely flow in and out through ports and regulating movement of beads, and is configured to firmly fix positioning lock bars to an outer surface of the vacuum pad. Thereby, when a patient wears the vacuum pad applied to the medical positioner, the beads held in the vacuum pad are prevented from being lopsided. The beads are grouped in cell units by partitions, so that movement of the beads from a designated cell to the neighboring cell through the ports is controlled. When the patient is examined using medical equipment, the medical positioner freely and accurately corrects a posture of the patient wearing the vacuum pad for diagnosis or treatment, and maintains the corrected posture to enhance accuracy of the diagnosis or treatment carried out through the medical equipment.

10 Claims, 8 Drawing Sheets

FOREIGN PATENT DOCUMENTS

| | | |
|---|---|---|
| JP | 2003-534047 | 11/2003 |
| JP | 2008-033074 | 2/2008 |
| JP | 2009-112380 | 5/2009 |
| WO | 92/04880 | 4/1992 |
| WO | 00/61038 | 10/2000 |
| WO | 2006/081412 | 8/2006 |

* cited by examiner

MEDICAL POSITIONER HAVING IMMOBILIZER FUNCTION

CROSS-REFERENCE TO RELATED APPLICATION

This application claims the benefit of Korean Patent Application Nos. 2009-0061167 filed Jul. 6, 2009 and 2010-0019735 filed Mar. 5, 2010, the disclosure of which is hereby incorporated herein by reference in its entirety.

BACKGROUND OF THE INVENTION

1. Field of the Invention

The present invention relates to a medical positioner having an immobilizer function. More particularly, the present invention relates to a medical positioner having an immobilizer function, which freely and accurately corrects a patient's posture on an examination table for diagnosis or treatment in an immobile posture, and maintains the corrected posture to enhance accuracy of the diagnosis or treatment carried out through medical equipment.

2. Description of the Related Art

Medical equipment (e.g. a Magnetic Resonance Imaging (MRI) scanner, a Computerized Axial Tomography (CT) scanner, X-ray equipment, an ultrasound scanner, a linear accelerator for radiotheraphy, etc.) for diagnosis and treatment is equipped with an examination table for a patient such that the patient can assume a stable posture. A medical positioner for restricting the patient's freedom to enhance accuracy of the diagnosis and treatment in a stable posture is used for such an examination table.

The medical positioner employs a belt fixed to the examination table to immobilize the patient, or a detachable vacuum pad. The immobilization based on the belt fails to properly cope with patients who have different physical conditions, and thus has low applicability.

For this reason, the detachable vacuum pad has been frequently used, because the detachable vacuum pad is smoothly deformed along a physical line of the patient to be able to properly cope with various physical conditions of patients.

This detachable vacuum pad is provided with a positioning lock bar having holes, and the examination table is provided with pins so as to be fitted into the holes of the lock bar. The lock bar is attached to an outer surface of the vacuum pad by an adhesive, or the like.

However, this detachable vacuum pad is formed of synthetic fiber, and the positioning lock bar is formed of rigid plastic. As such, when the lock bar is attached to an outer surface of the vacuum pad by an adhesive, or the like, the lock bar often fails to be firmly attached.

Thus, when an examination position of the vacuum pad is set by inserting the pins of the examination table into the holes of the positioning lock bar fixedly attached to the vacuum pad in the state where the patient wears the vacuum pad, the lock bar is frequently separated from the vacuum pad. In this case, an error is made in positioning and fixing the vacuum pad for the diagnosis and treatment, and thus the accuracy of the diagnosis and treatment of the patient using the medical examination equipment is considerably decreased.

SUMMARY OF THE INVENTION

Aspects of the present invention provide a medical positioner having an immobilizer function, which can firmly fix positioning lock bars to the outer surface of a vacuum pad, thereby making it possible to freely and accurately immobilize a patient wearing the vacuum pad on an examination table in a constant posture, and to enhance accuracy of diagnosis or treatment carried out through medical equipment.

Aspects of the present invention also provide a medical positioner having an immobilizer function, which includes a vacuum pad allowing air to freely flow in and out through ports and regulating movement of beads for correcting the posture of a patient, thereby making it possible to prevent the beads held in the vacuum pad applied to the medical positioner from being lopsided, to group the beads in cell units using partitions, and to control movement of the beads from a designated cell to the neighboring cell through the ports.

According to an embodiment of the present invention, a medical positioner having an immobilizer function includes: a vacuum pad having an air nozzle, a plurality of buckle assemblies, each of which has female and male members, and beads held therein, and forming an air cushion when air is filled, and allowing a body of a patient to be immobilized in cooperation with the beads under vacuum when the air is discharged; at least one positioning lock bar having holes, into which positioning pins of an examination table constituting a set together with medical equipment are fitted, and fixed to an outer surface of the vacuum pad; and at least one fixture bar fixed to an inner surface of the vacuum pad corresponding to a position of the lock bar. When an adhesive for fixing the lock bar and the fixture bar is applied to the outer and inner surfaces of the vacuum pad, the fixture bar is mutually adhered to the lock bar by the adhesive absorbed into the vacuum pad.

According to an embodiment of the present invention, the vacuum pad may form the air cushion by the air filling, and be coupled to an auxiliary airbag supporting a specific posture of the patient who wears the vacuum pad.

According to an embodiment of the present invention, the vacuum pad may include a strapped ring, and the auxiliary airbag may include a strapped hook hooked on the strapped ring.

According to an embodiment of the present invention, the vacuum pad may be formed of a twofold wrap having upper and lower wraps, be partitioned into a plurality of cells with partitions sealed by thermal fusion of an edge and intermediate portions of the twofold wrap, and include ports through which the air flows. Each port may be formed in each partition such that the cells communicate with each other.

According to an embodiment of the present invention, the partition may be formed by the thermal fusion between the upper and lower wraps, and each port may be formed in a part of each partition which is not subjected to the thermal fusion between the upper and lower wraps.

According to an embodiment of the present invention, each port may include a filter installed therein so as to selectively pass the air and block the beads.

According to an embodiment of the present invention, as the partitions move farther away from the air nozzle, the port and the filter may have gradually increasing diameters.

According to an embodiment of the present invention, the filter may include a sponge freely contracted such that the vacuum pad does not pinch the body of the patient under vacuum.

According to an embodiment of the present invention, the sponge may have a cylindrical shape, have a diameter 1.5 times that of the port, and be mounted in the port in the state where an intermediate portion thereof is contracted.

According to an embodiment of the present invention, each bead may have a diameter of 2 mm or more, and the sponge may have a maximum mesh size of 1.5 mm.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
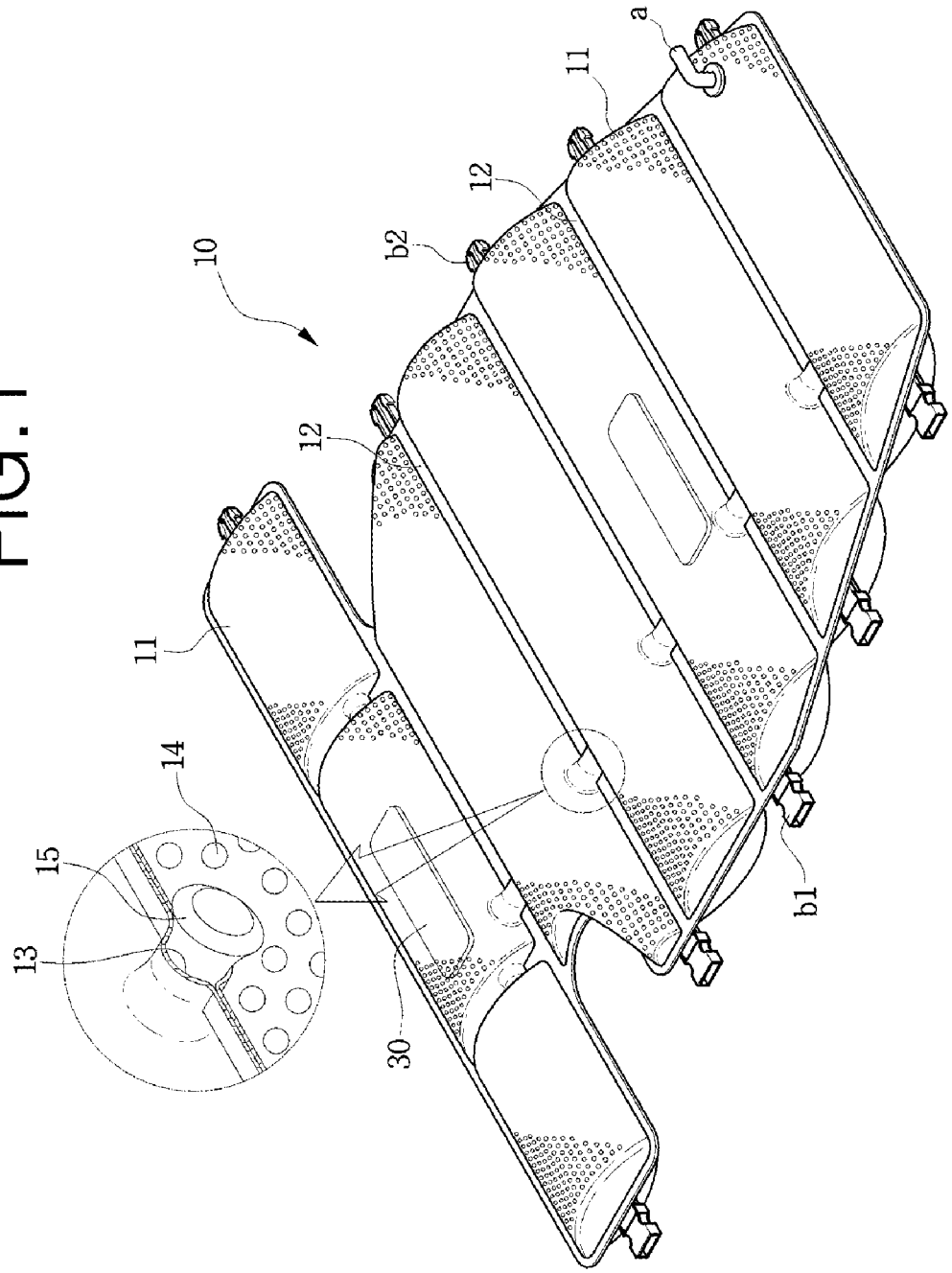
FIG. 1 is a perspective view illustrating the structure of a medical positioner having an immobilizer function according to an exemplary embodiment of the present invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Figure 2:
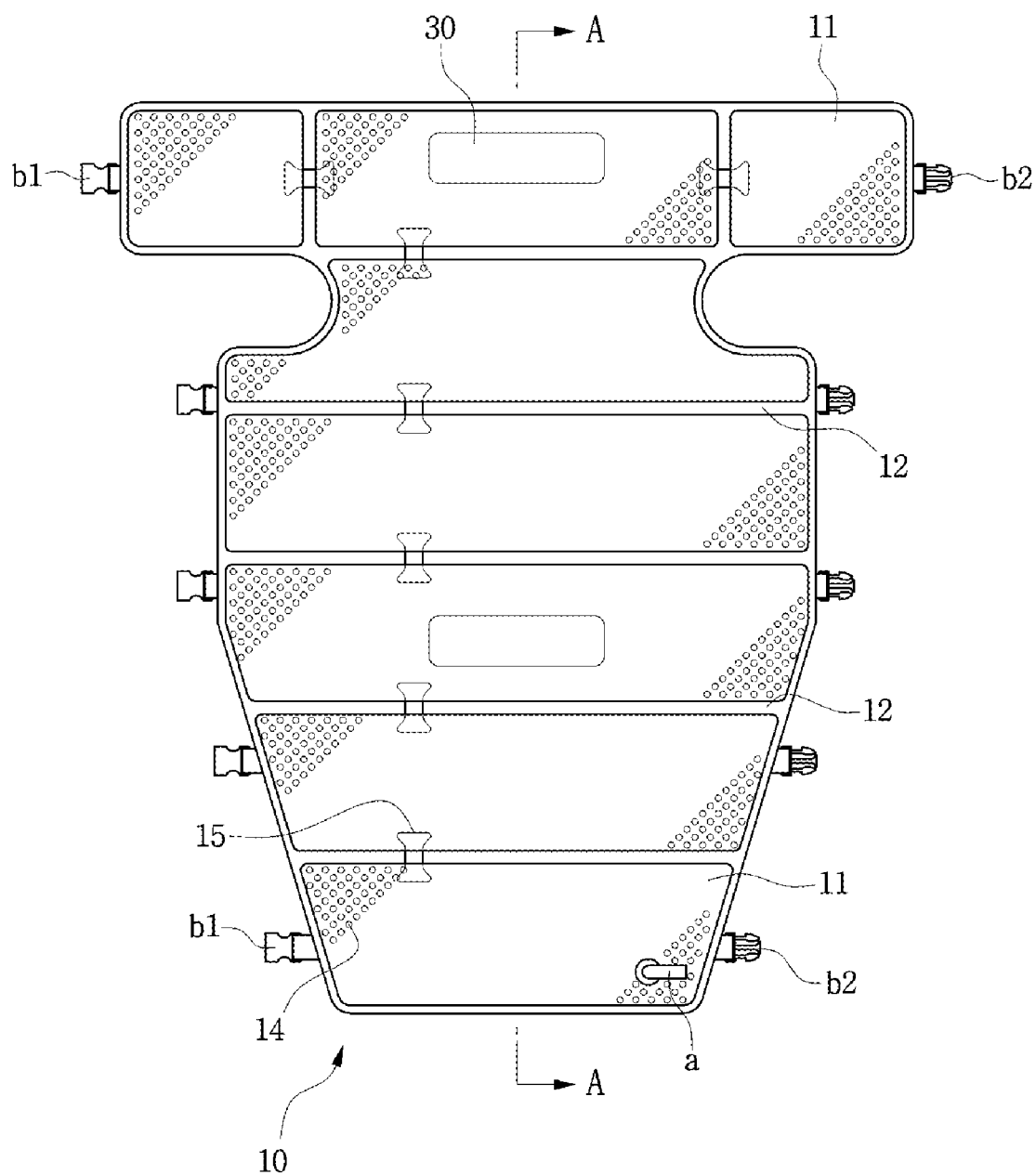
FIG. 2 is a developed plan view illustrating the structure of a medical positioner having an immobilizer function according to an exemplary embodiment of the present invention.
Figure 3:
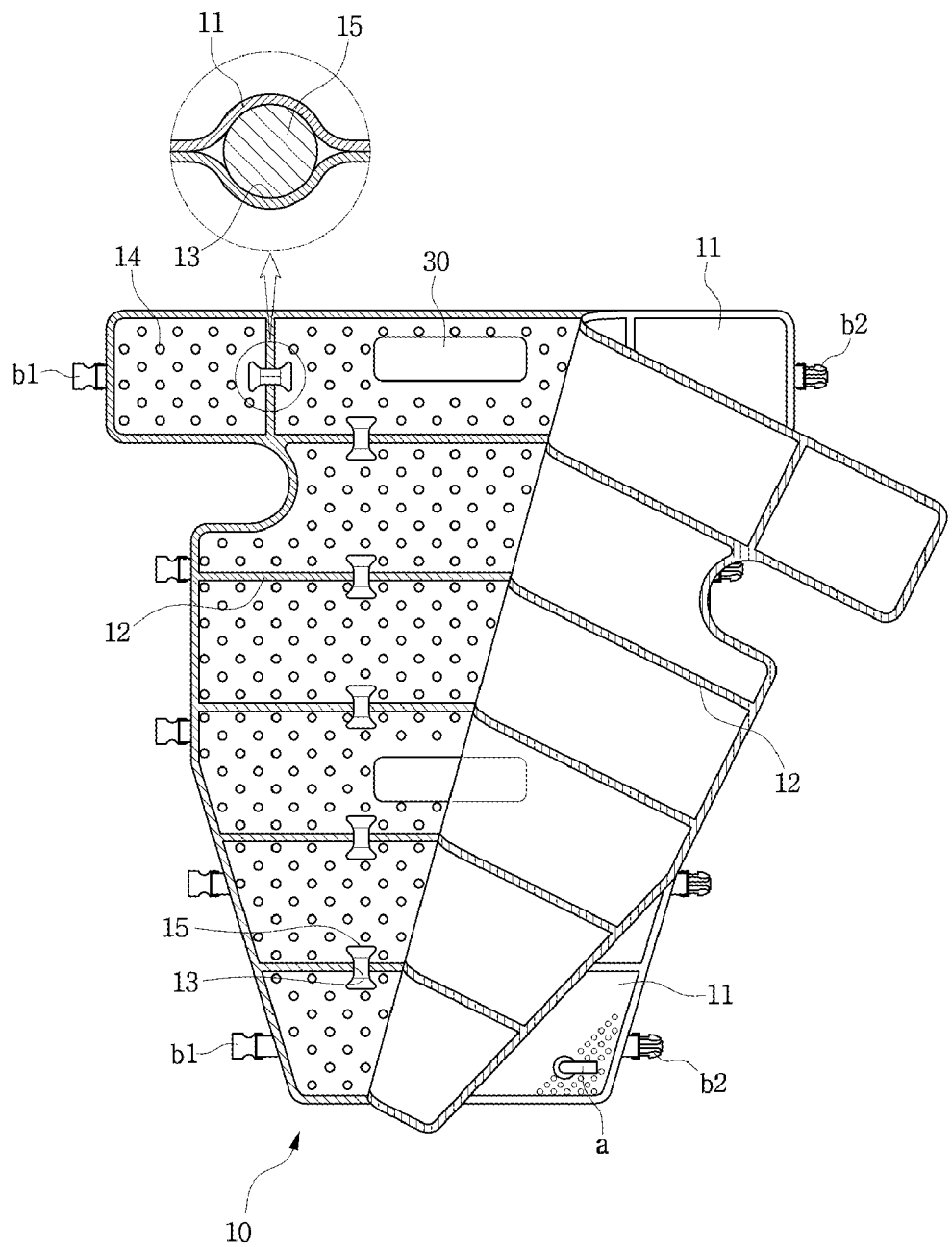
FIG. 3 is a partial cutaway perspective view illustrating the structure of a medical positioner having an immobilizer function according to an exemplary embodiment of the present invention.
Figure 4:
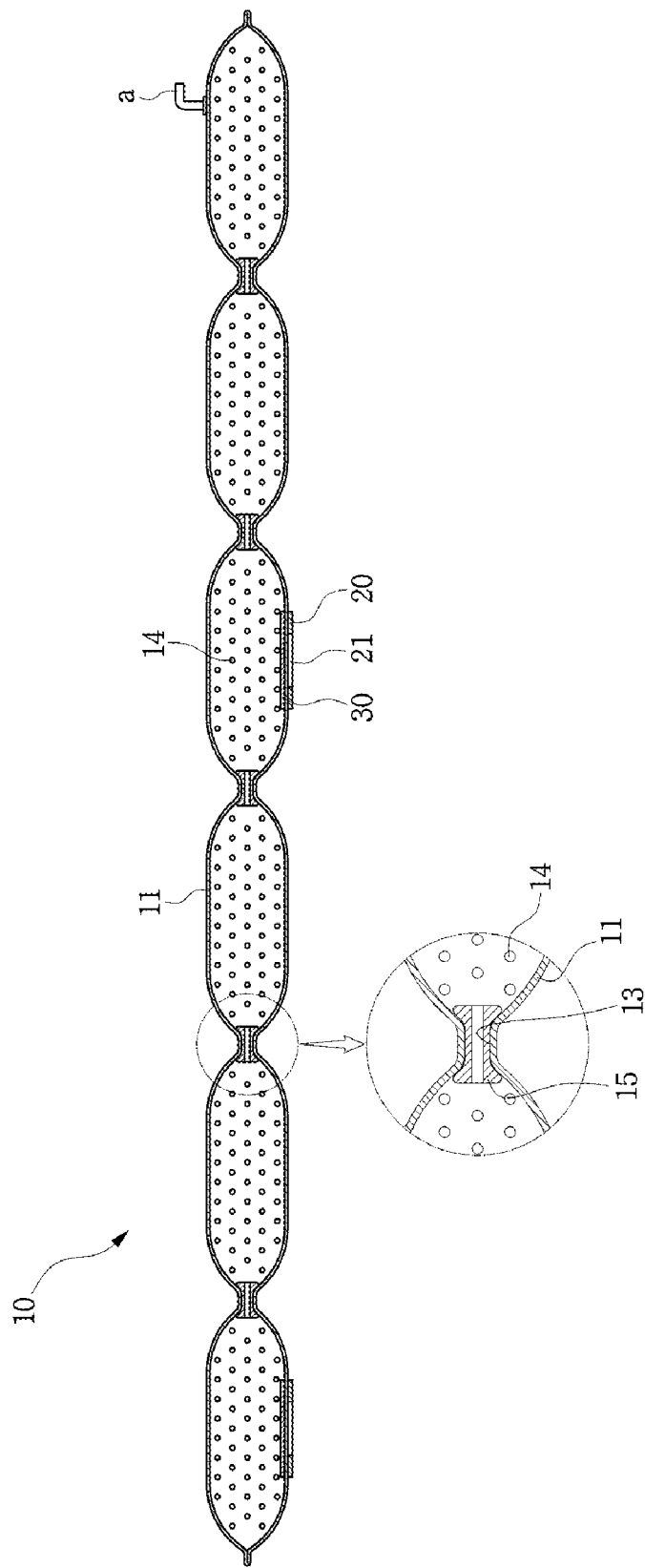
FIG. 4 is a cross-sectional view taken along line A-A of FIG. 2.

FIG. 1 is a perspective view illustrating the structure of a medical positioner having an immobilizer function according to an exemplary embodiment of the present invention. FIG. 2 is a developed plan view illustrating the structure of a medical positioner having an immobilizer function according to an exemplary embodiment of the present invention. FIG. 3 is a partial cutaway perspective view illustrating the structure of a medical positioner having an immobilizer function according to an exemplary embodiment of the present invention. FIG. 4 is a cross-sectional view taken along line A-A of FIG. 2.

Figure 5:
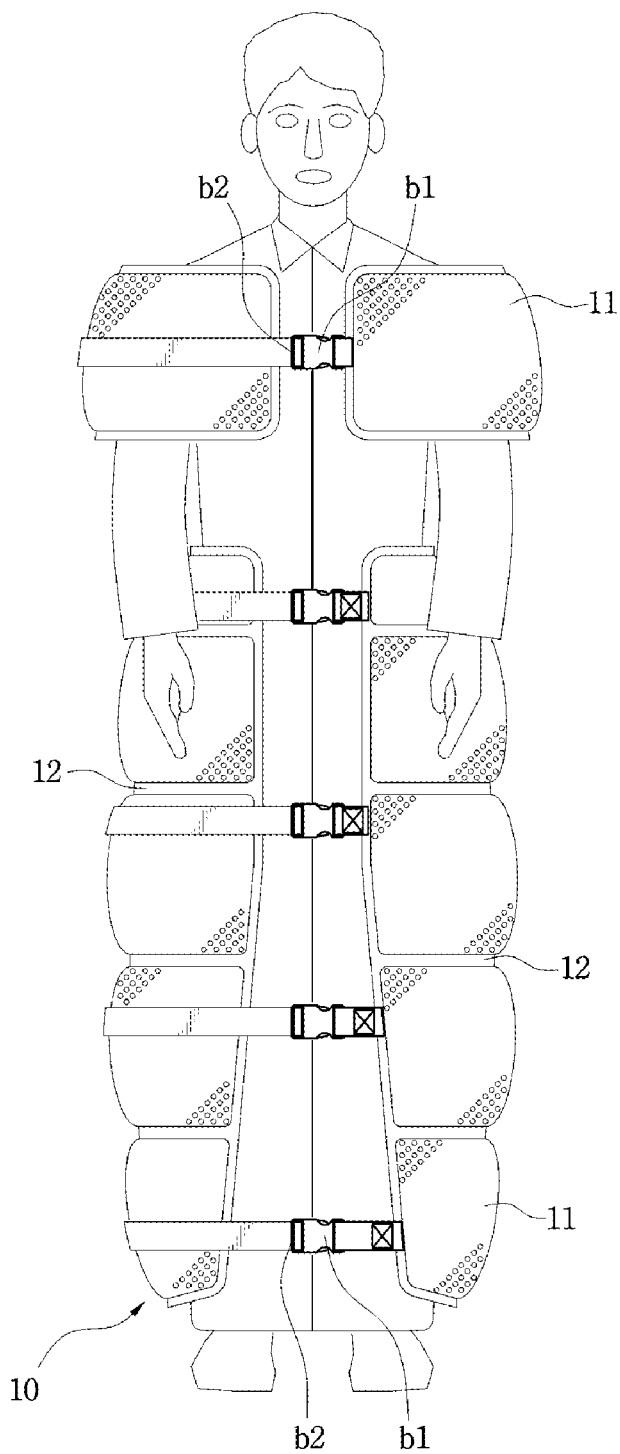
FIG. 5 is a perspective view illustrating the state where a patient wears a medical positioner having an immobilizer function according to an exemplary embodiment of the present invention.
Figure 6:
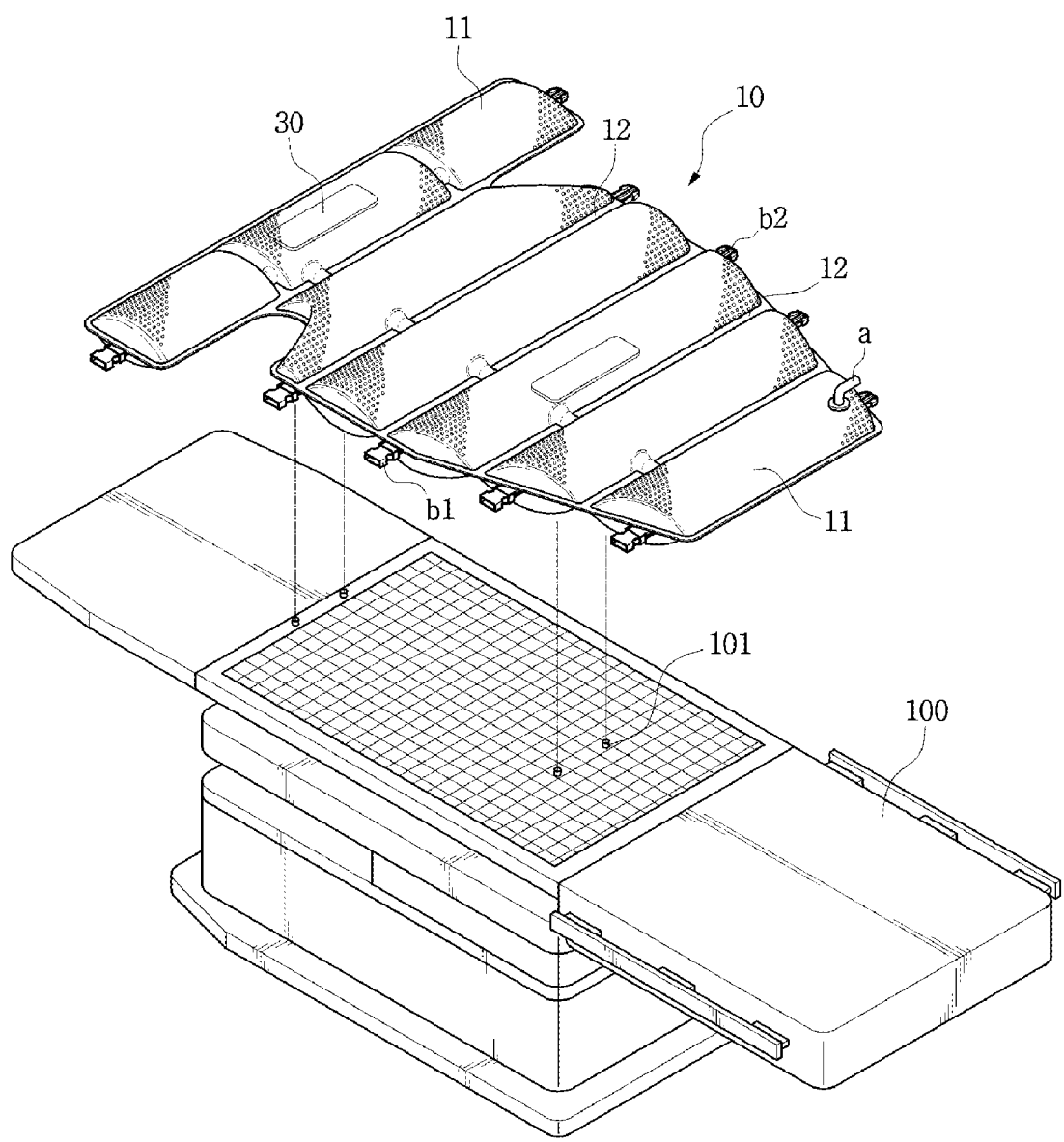
FIG. 6 illustrates the state when an examination table of medical equipment is separated from a medical positioner having an immobilizer function according to an exemplary embodiment of the present invention.
Figure 7:
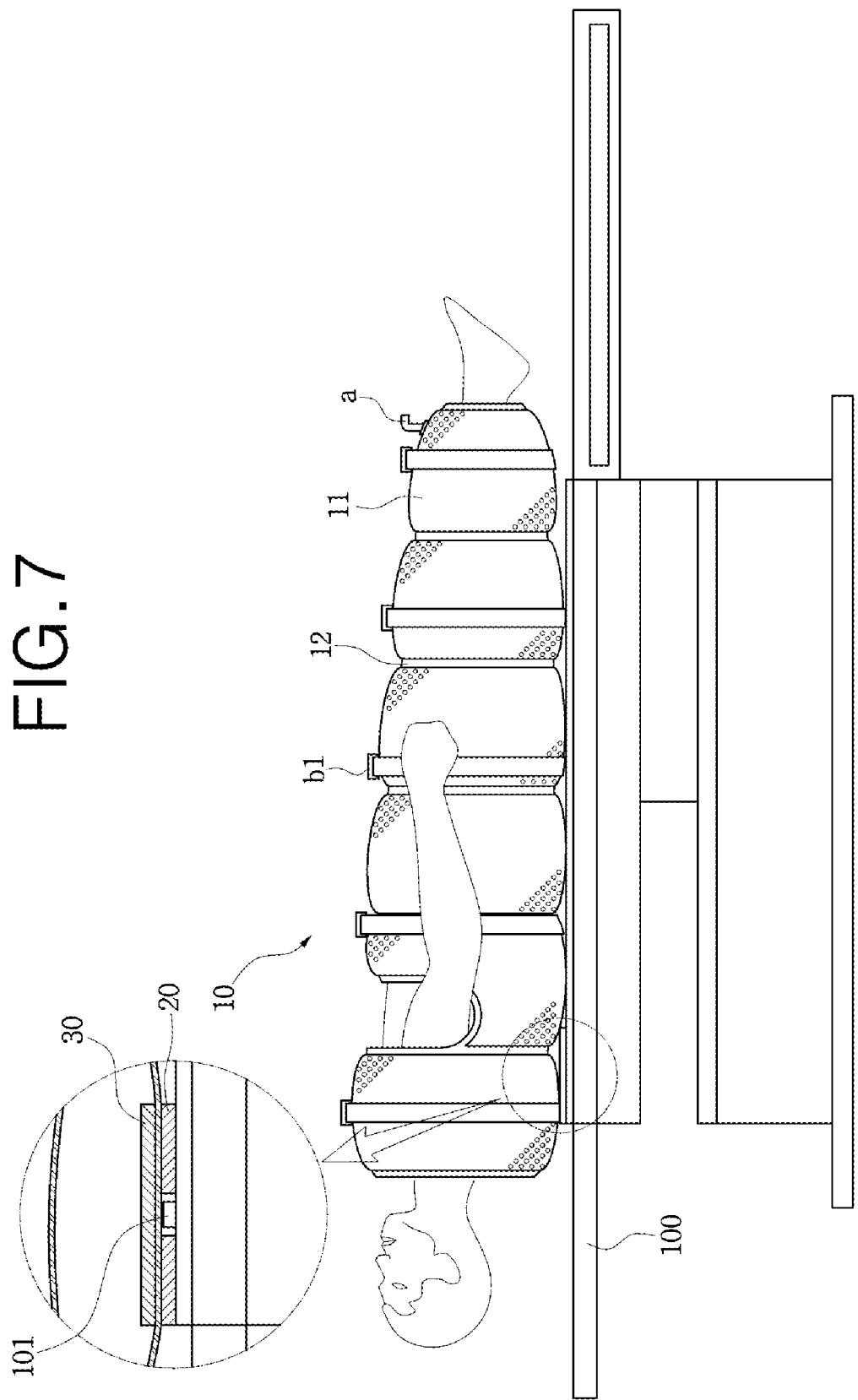
FIG. 7 is a side view illustrating the state when a patient wearing a medical positioner having an immobilizer function according to an exemplary embodiment of the present invention is immobilized on an examination table of medical equipment in order to set a diagnosis or treatment position.

FIG. 5 is a perspective view illustrating the state where a patient wears a medical positioner having an immobilizer function according to an exemplary embodiment of the present invention. FIG. 6 illustrates the state when an examination table of medical equipment is separated from a medical positioner having an immobilizer function according to an exemplary embodiment of the present invention. FIG. 7 is a side view illustrating the state when a patient wearing a medical positioner having an immobilizer function according to an exemplary embodiment of the present invention is immobilized on an examination table of medical equipment in order to decide a diagnosis or treatment position.

As illustrated in FIGS. 1 through 7, a medical positioner having an immobilizer function according to an exemplary embodiment of the present invention includes a vacuum pad 10, at least one lock bar 20, and at least one fixture bar 30.

The vacuum pad 10 is put on by a patient so as not only to correct a posture of the patient such that the patient lies on an examination table constituting a set together with medical equipment (e.g. a Magnetic Resonance Imaging (MRI) scanner, a Computerized Axial Tomography (CT) scanner, X-ray equipment, an ultrasound scanner, a linear accelerator for radiotheraphy, etc.) to be diagnosed or treated through the medical equipment, but also to maintain the corrected posture. The vacuum pad 10 is provided with an air nozzle a and a plurality of buckle assemblies, each of which has female and male members b1 and b2. The vacuum pad 10 forms an air cushion when air is filled through the air nozzle a.

Here, the vacuum pad 10 is made of a twofold wrap 11 of soft synthetic resin which is constituted of upper and lower wraps. The vacuum pad 10 is formed in a tubular shape by sealing an edge of the wrap 11 through sewing or thermal fusion. To connect the upper and lower wraps, the wrap 11 has a plurality of partitions 12 formed by thermal fusion of intermediate portions of the wrap 11 like the edge of the wrap 11.

The partitions 12 are discontinuously formed, and at least one port 13 through which air flows is formed in each partition 12, so that a plurality of cells are formed by the partitions 12, thereby forming a network structure with the port 13.

It is essential to provide the one air nozzle a at one side of the vacuum pad 10 in order to supply or discharge the air. This air is supplied by a compressor, and discharged by a suction unit.

As described above, the number of air nozzle a is limited to one, because the cells formed by the partitions 12 communicate with each other through the ports 13.

When the air flows in or out at a high speed through the ports 13, beads 14 also tend to move together with the air. In practice, this can undermine a function of the partitions 12.

In the present invention, to reinforce the function of the partitions 12 distributing the beads 14 at a proper fraction, a filter 15 selectively passing only the air is installed in a space, i.e. the port 13, between the partitions. The filter 15 is characterized by a spongy material having a high degree of freedom of shape such that the patient is not pinched when lying on the filter 15.

In other words, the filter 15 is preferably a sponge, through which the air can freely pass and the passage of the bead 14 is selectively controlled.

The sponge used as the filter 15 is formed in a cylindrical shape having a predetermined diameter, which is at least 1.5 times, preferably twice or more, the diameter of the port 13 formed when the air is maximally filled in the vacuum pad 10.

Since the sponge used as the filter 15 can be contracted, the sponge is inserted into the port 13 without trouble even though the diameter of the sponge is larger than that of the port 13. Rather, since the diameter of the sponge is larger than that of the port 13, the sponge is prevented from being unintentionally separated from the port 13.

That is, the sponge used as the filter 15 is contracted and press-fitted into the port 13.

Here, the shape of the sponge used as the filter 15 is not limited to the cylindrical shape, because the sponge used as the filter 15 has a high degree of freedom of shape, is not easily separated from the port 13 by an elastic force if a diameter thereof is not smaller than that of the port 13, and allows of the passage of the air but not the beads 14.

Thus, it is not necessary to fix the sponge used as the filter 15 to the port 13 using a separate adhesive. Of course, only when the sponge used as the filter 15 has a length of at least 1.5 cm, is the sponge not easily separated from the port 13 in a lengthwise direction.

Since the sponge used as the filter 15 has a cushion in itself in the state where the air is completely discharged from the vacuum pad 10, the sponge is never regarded as an obstacle, for instance an outward protrusion, when viewed from the outside, and particularly is convenient because it does not pinch the body of the patient.

Alternatively, the vacuum pad 10 may be formed by molding.

Considering that the diameter of the beads 14 is typically 2 mm or more, the size of meshes of the sponge is preferably a maximum of 1.5 mm, and a minimum of 0.5 mm for free passage of the air.

Meanwhile, according to an exemplary embodiment of the present invention, the one air nozzle a is installed on the vacuum pad 10. Since the air is sequentially supplied to each partition 12 through the air nozzle a, the supply of the air may be reduced in proportion to a distance from the air nozzle a to the partition 12.

Thus, as the partition 12 moves farther away from the air nozzle a, the diameter of the port 13 or the sponge used as the filter 15 needs to be increased gradually.

The lock bar 20 is provided with holes 21, into which positioning pins 101 of the examination table 100 constituting a set together with the medical equipment are fitted. The lock bar 20 is adhered to an outer surface of the vacuum pad 10 through an adhesive.

The fixture bar 30 is adhered to an inner surface of the vacuum pad 10, i.e. an inner surface of the lower wrap constituting the twofold wrap 11, corresponding to the position of the lock bar 20 through an adhesive.

Here, the fixture bar 30 is mutually adhered to the lock bar 20 through the adhesive absorbed to the vacuum pad 10 when the adhesive for fixedly adhering the lock bar 20 and the fixture bar 30 is applied to the outer and inner surfaces of the vacuum pad 10.

In detail, the vacuum pad 10 is formed of a soft synthetic resin, while the lock bar 20 and the fixture bar 30 are formed of a hard synthetic resin such as plastic. In the state where the adhesive is applied to the outer and inner surfaces of the vacuum pad 10, the lock bar 20 is adhered to the outer surface of the vacuum pad 10, and the fixture bar 30 is adhered to the inner surface of the vacuum pad 10. Afterwards, the lock bar 20 and the fixture bar 30 are pressurized.

Thereby, the adhesive applied to the outer and inner surfaces of the vacuum pad 10 is absorbed into the vacuum pad 10, so that the lock bar 20 and the fixture bar 30 can be mutually adhered by the absorption of the adhesive, and thus the lock bar 20 can maintain firm adhesion to the outer surface of the vacuum pad 10 with the aid of the fixture bar 30.

As described above, after the lock bar 20 is firmly adhered to the outer surface of the vacuum pad 10, the air is injected into the vacuum pad 10 through the air nozzle a, as illustrated in FIGS. 4 through 7.

Thereby, the vacuum pad 10 is partitioned into the cells with the partitions 12. Since each partition 12 has at least one port 13 in which the sponge used as the filter 15 is mounted, the air injected into the vacuum pad 10 through the air nozzle a is supplied into all the cells partitioned with the partitions 12, and the beads 14 filled in each cell are prevented from moving to another cell by the filter 15.

Here, since the beads 14 are distributed to each of the cells partitioned with the partitions 12 at a proper rate, the beads 14 are collected to one side when the vacuum pad 10 stands erect, whereas the air can be freely supplied to or discharged through the cells partitioned with the partitions 12 because the filter 15 has a predetermined mesh size.

Thus, when a compressor is connected to the air nozzle a, and driven to perform air injection into the cells partitioned with the partitions 12, the vacuum pad 10 is expanded to a predetermined volume. This expanded vacuum pad 10 is put on the patient using the female and male members b1 and b2.

Next, the patient wearing the vacuum pad 10 expanded to a predetermined volume by the air injection is laid on the examination table 100, and then is moved to fit the positioning pins 101 of the examination table 100 into the holes 21 of the lock bars 20 of the vacuum pad 10.

Thereby, a diagnosis or treatment position of the patient wearing the vacuum pad 10 is determined on the examination table 100.

When the diagnosis or treatment position of the patient is determined on the examination table 100, a suction unit is connected to the air nozzle a of the vacuum pad 10 put on the patient, and is driven to discharge a predetermined amount of air from the vacuum pad 10 partitioned into the plurality of cells with the partitions 12.

In this manner, when the air is discharged from the vacuum pad 10 partitioned into the plurality of cells with the partitions 12, a posture of the patient can be accurately corrected according to the distribution rate of the beads 14. Thereby, when the diagnosis or treatment corresponding to the medical service using the medical equipment is carried out, the diagnosis or treatment can be precisely carried out.

Figure 8:
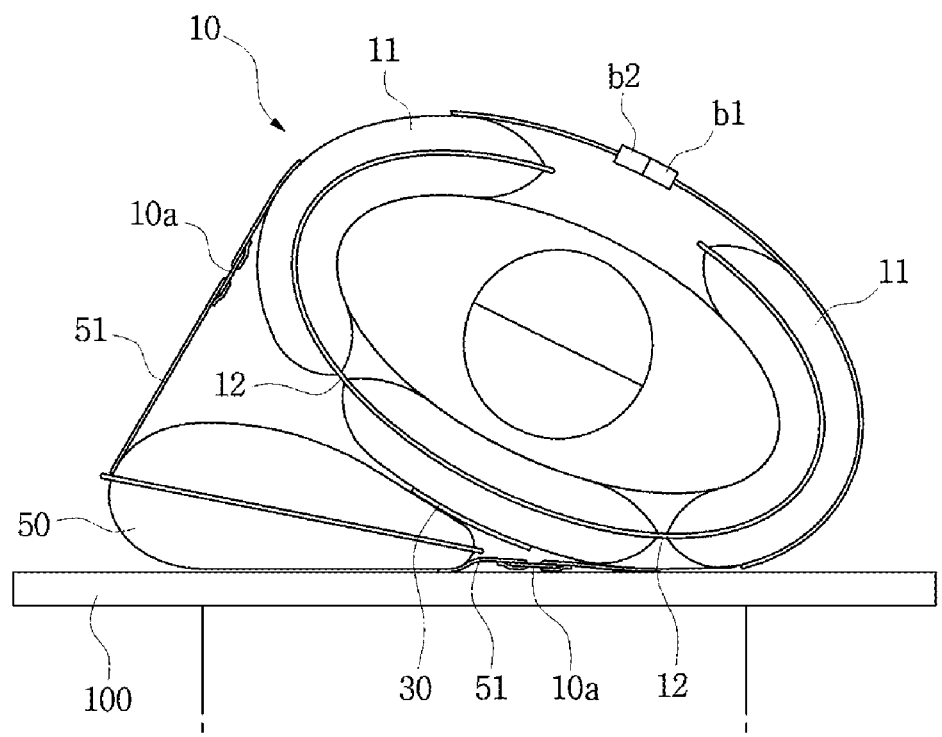
FIG. 8 illustrates the state where an auxiliary airbag capable of supporting a specific posture is coupled to a vacuum pad according to another exemplary embodiment of the present invention.

Meanwhile, FIG. 8 illustrates the state where an auxiliary airbag 50 capable of supporting a specific posture is coupled to a vacuum pad 10 according to another exemplary embodiment of the present invention.

The vacuum pad 10 is provided with a strapped ring 10a on one side thereof, and the auxiliary airbag 50 is provided with a strapped hook 51 on one side thereof. Thus, the auxiliary airbag 50 is coupled to the vacuum pad 10 by connecting the strapped ring 10a and the strapped hook 51.

Thereby, when the patient wearing the vacuum pad 10 assumes a specific posture on the examination table 100, for instance an inclined posture where one shoulder of the patient is raised, the auxiliary back 50 supports the specific posture, so that it is possible to enhance efficiency of the diagnosis or treatment service.

As described above, a medical positioner includes a vacuum pad allowing air to freely flow in and out through ports and regulating the movement of beads, and is configured to firmly fix the positioning lock bars to the outer surface of the vacuum pad. Thereby, when the patient wears the vacuum pad applied to the medical positioner, the beads held in the vacuum pad are prevented from being lopsided. The beads are grouped in cell units by the partitions, so that movement of the beads from a designated cell to the neighboring cell through the ports is controlled. When the patient is examined by the medical equipment, the medical positioner freely and accurately corrects the posture of the patient wearing the vacuum pad for the diagnosis or treatment, and maintains the corrected posture to enhance accuracy of the diagnosis or treatment carried out through the medical equipment.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A medical positioner having an immobilizer function, comprising: a vacuum pad having an air nozzle, a plurality of buckle assemblies, each of which has female and male members, and beads held therein, and forming an air cushion when air is filled, and configured for allowing a body of a patient to be immobilized in cooperation with the beads under vacuum when the air is discharged;

at least one positioning lock bar having holes, into which positioning pins of an examination table constituting a set together with medical equipment are fitted, and fixed to an outer surface of the vacuum pad; and at least one fixture bar fixed to an inner surface of the vacuum pad corresponding to a position of the lock bar wherein, when an adhesive for fixing the lock bar and the fixture bar is applied to the outer and inner surfaces of the vacuum pad, the fixture bar is mutually adhered to the lock bar by the adhesive absorbed into the vacuum pad.

2. The medical positioner according to claim 1, wherein the vacuum pad is formed of a twofold wrap having upper and lower wraps, is partitioned into a plurality of cells with partitions sealed by thermal fusion of an edge and intermediate portions of the twofold wrap, and includes ports through which the air flows, wherein each port is formed in each partition such that the cells communicate with each other.

3. The medical positioner according to claim 2, wherein each port includes a filter installed therein so as to selectively pass the air and block the beads.

4. The medical positioner according to claim 3, wherein the filter includes a sponge freely contracting such that the vacuum pad does not pinch the body of the patient under vacuum.

5. The medical positioner according to claim 4, wherein the sponge has a cylindrical shape, has a diameter 1.5 times that of the port, and is mounted in the port in a state where an intermediate portion thereof is contracted.

6. The medical positioner according to claim 5, wherein each bead has a diameter of 2 mm or more, and the sponge has a maximum mesh size of 1.5 mm.

7. The medical positioner according to claim 3, wherein, as the partitions move farther away from the air nozzle, the port and the filter have gradually increasing diameters.

8. The medical positioner according to claim 2, wherein the partition is formed by the thermal fusion between the upper and lower wraps and each port is formed in a part of each partition which is not subjected to the thermal fusion between the upper and lower wraps.

9. The medical positioner according to claim 1, wherein the vacuum pad is coupled to an auxiliary airbag adapted to support a specific posture of the patient who wears the vacuum pad.

10. The medical positioner according to claim 9, wherein the vacuum pad includes a strapped ring, and the auxiliary airbag includes a strapped hook hooked on the strapped ring.

* * * * *